(12) United States Patent
Goel et al.

(10) Patent No.: US 11,302,427 B2
(45) Date of Patent: Apr. 12, 2022

(54) SYSTEM AND METHOD FOR MANAGING MEDICINE PRESCRIPTIONS

(71) Applicant: Anoj Goel, Saint Louis, MO (US)

(72) Inventors: Anoj Goel, Saint Louis, MO (US);
Anmol Goel, Saint Louis, MO (US);
Manoj Prakash Goel, Saratoga, CA (US)

(*) Notice: Subject to any disclaimer, the term of this patent is extended or adjusted under 35 U.S.C. 154(b) by 526 days.

(21) Appl. No.: 15/600,722

(22) Filed: May 20, 2017

(65) Prior Publication Data

US 2017/0337346 A1    Nov. 23, 2017

Related U.S. Application Data

(60) Provisional application No. 62/339,862, filed on May 21, 2016.

(51) Int. Cl.
| | | |
|---|---|---|
| *G16H 10/60* | (2018.01) | |
| *G16H 40/20* | (2018.01) | |
| *G16H 20/10* | (2018.01) | |
| *G16H 70/40* | (2018.01) | |
| *G06Q 10/10* | (2012.01) | |

(52) U.S. Cl.
CPC ............. *G16H 10/60* (2018.01); *G06Q 10/10* (2013.01); *G16H 20/10* (2018.01); *G16H 40/20* (2018.01); *G16H 70/40* (2018.01)

(58) Field of Classification Search
CPC combination set(s) only.
See application file for complete search history.

(56) References Cited

U.S. PATENT DOCUMENTS

| | | | |
|---|---|---|---|
| 2009/0043609 | A1* | 2/2009 | Nadas et al. |
| 2014/0006055 | A1* | 1/2014 | Seraly et al. |
| 2014/0330588 | A1* | 11/2014 | Epstein et al. |
| 2016/0378950 | A1* | 12/2016 | Reiner |
| 2017/0032101 | A1* | 2/2017 | Skoda |
| 2017/0213010 | A1* | 7/2017 | Sucilla et al. |

\* cited by examiner

*Primary Examiner* — Michael Tomaszewski
*Assistant Examiner* — William T. Monticello

(57) ABSTRACT

The present disclosure envisages a system and method for management of medical prescriptions, and particularly management of medical prescription refills. The present disclosure envisages a centralized system termed 'RxRefillHub' that receives and analyzes the medical prescriptions, and releases only one refill for each of the medical prescriptions at a time. The RxRefillHub also provides healthcare providers and patients with seamless access to the medical prescriptions thereby providing for easy modification of the medical prescriptions at any point of time post generation. The RxRefillHub provides ready access to all the information corresponding to the medical prescriptions generated for a specific patient, current refill status, medication history and details of the prescribing physician. The RxRefillHub also generates alerts when a term associated with a refill is nearing termination.

5 Claims, 3 Drawing Sheets

SYSTEM AND METHOD FOR MANAGING MEDICINE PRESCRIPTIONS

CROSS-REFERENCE TO RELATED APPLICATION

The embodiments herein claim the priority of the U.S. Provisional Patent Application with Ser. No. 62/339,862 filed on May 21, 2016, with the title "A SYSTEM AND METHOD FOR MANAGING MEDICINE PRESCRIPTION", and the contents of which is included entirely as reference herein.

BACKGROUND

Technical Field

The present disclosure is generally related to medical prescription management. The present disclosure is particularly related to Management of Medicine prescription refills. The present disclosure is more particularly related to improving safety and accuracy of Medicine prescription refills by establishing an RxRefillHub to centralize and standardize handling of refills.

Description of the Related Art

Medicine prescriptions are required by authorities for proper dispensing of medications at the order of healthcare providers. Medicine prescriptions are generated and handled by a plurality of methods including paper prescriptions, verbal and electronic prescriptions transmitted by fax and other online methods. Many Medication prescriptions are accompanied by specified number of refills at the discretion of a corresponding prescribing authority. The number of prescription refills could be anywhere from 1-11 at the discretion of prescribing authority. Further, the number of prescription refills is also influenced by factors such as insurance benefits, diagnosis and the like. Due to the variable numbers of refills assigned to each of the prescriptions, many of the refills expire at different days and/or months for an individual patient. Renewal of these refills is time consuming, and is prone to errors and omissions given the functionalities and implementation of prior art refill management systems.

The Medicine prescription refills are typically handled by a plurality of organizations including local, hospital and mail order pharmacies. Further, several government and insurance organizations also receive these transmitted Medicine prescription refills in the evolving healthcare system. Typically, the Medicine prescription refills are currently stored in a decentralized manner by the final contact pharmacy or processing entity.

Once Medicine prescription refills are received and stored by the processing entity, either, if the healthcare provider decides to delete or modify the treatment, or if the patient does not need the prescription refill anymore or if the insurance company modifies the formulary prescription coverage, the refills are not available to a healthcare provider for any future modifications.

Once Medicine prescription refills are received and stored by the processing entity, most refills are left active with the final holding entity. If the medication is no longer required or appropriate, these refills are many times filled by the patient in error. The current system of storage and handling of prescription refills and inability of physician to modify them due to a decentralized system often results in incorrect dispensing of refills. Further, once a Medicine prescription refill is stored in the pharmacy, it is not available to the patient for transfer to another pharmacy, thereby contributing to inconsistent communication between the patient and prescriber, prescriber and pharmacy, insurance formulary issues and ultimately, delay or an error in treatment.

Once a Medicine prescription refill is stored in the pharmacy, it is difficult to analyze the medicine prescription for drug-drug interactions, duplication of treatment, incorrect dosing unless all the prescribed refills are performed by a single prescribing person, filled at a single pharmacy, and adjudicated by single payer, thus exposing the patient to significant risks and side effects.

Once a Medicine prescription refill is stored in the pharmacy, it is difficult to analyze it for payer formulary changes, which results in denial of prescription refills, unnecessary delay in refills, denial of treatment, leading to additional work at multiple levels for the prescriber, pharmacy, payer or patient while exposing patient to additional risks from a delay in treatment.

The current alert and refill system available for managing medicine prescriptions is tedious and prone to errors. It contributes to delays in treatment, an increase in healthcare costs and stress or dissatisfaction among healthcare providers, patients and payers. Many third-party organizations are involved in monitoring of appropriate utilization and safety of prescribed medications. The current medication associated risk monitoring system is fragmented and administered by different payers based on non-uniform criteria, funding availability and is not available to patients who are not enrolled in organized healthcare system, or get their care in a mixed payer system.

The current medication associated risk monitoring system places an unnecessary burden on prescribing healthcare providers, payers, patients, pharmacies and is prone to errors at multiple levels, contributing to an increased risk of medication related errors. The current medication associated risk monitoring system also contributes to the increased cost of therapy for the patients, government and private payers by allowing dispensing of often unnecessary, ineffective, obsolete and sometime dangerous therapies.

Hence, there is a need for a system and method for managing Medicine prescription refills. Furthermore, there is a need for a system and method that reduces the risks associated with medicine prescription refills, and improves the process of Managing medicine prescription refills. Also, there is a need for a system to optimize cost efficient, safe delivery method of prescription refills.

Objects

The present disclosure envisages a system and method for Managing Medicine prescription refills, transmission and retrieval thereof.

The primary object of the present disclosure is to create a clearing house for Medicine prescription refills named RxRefillHub.

Yet another object of the present disclosure is to reduce errors related to Medicine prescription refills by using RxRefillHub.

Yet another object of the present disclosure is to improve safety of Medicine prescription refills by reducing duplication and appropriate disposition of pending refills by RxRefillHub.

Yet another object of the present disclosure is to improve cost efficiency related to Medicine prescription refills by RxRefillHub.

Yet another object of the present disclosure is to improve transparency of Medicine prescription refills in various healthcare settings by standardizing and streamlining of the processes by RxRefillHub.

Yet another object of the present disclosure is to provide medication associated risk monitoring system to, all patients regardless of payer preferences and availability of funds.

These and other objects and advantages of the present disclosure will become apparent from the following detailed description of RxRefillHub read in conjunction with the accompanying drawings.

SUMMARY

The present disclosure envisages a system and method for improving safety and accuracy of Medicine prescription refills. Typically, a Medicine prescription refill is generated by a healthcare provider. The Medicine prescription refill is based on current standards of prescriptions as defined by State and Federal laws. Once the healthcare provider generates a Medicine prescription refill, it is transmitted to the centralized system envisaged by the present disclosure (referred to as an RxRefillHub hereafter). The RxRefillHub stores the Medicine prescription refills in a secure and compliant environment. The RxRefillHub releases the Medicine prescription refill to the pharmacy on request, only one refill at a time. The healthcare provider would receive an alert, when the refills are approaching a predetermined level at the RxRefillHub. The RxRefillHub would generate any drug interaction based on concurrent prescriptions for the patient. The RxRefillHub would receive formulary updates, alerts and generate preferred formulary suggestions based on payer's preference and coverage.

The RxRefillHub would enable the healthcare providers to add, delete or modify unused existing prescriptions refills stored at RxRefillHub, when warranted by a change in patient condition, payer status, formulary change and drug-drug interactions. The RxRefillHub enables patients to update their user profile, healthcare provider preferences, insurance information and assign preferred pharmacies to fill the Medicine prescription. The RxRefillHub also enables the patients to update their formularies as well as allow communication to prescribing physicians and pharmacies about changes in the formularies and preferred drugs.

The RxRefillHub also enables urgent care and emergency healthcare providers to obtain single source current Medicine prescriptions, refill status, medication fill history and prescribing physician information in a compliant manner.

The RxRefillHub provides medication associated risk monitoring system to all patients regardless of payer preferences and availability of funds.

These and other aspects of the embodiments herein will be better appreciated and understood when considered in conjunction with the following description and the accompanying drawings. It should be understood, however, that the following description, while indicating the preferred embodiment and numerous specific details thereof, are given by way of illustration and not limitation. Certain changes and modifications could be implemented by one skilled in the art without deviating from the scope of the embodiments described herein, and the embodiments described herein should be construed as incorporating all such modifications.

BRIEF DESCRIPTION OF THE DRAWINGS

The other objects, features and advantages will occur to those skilled in the art from the following description of the preferred embodiment and the accompanying drawings in which.

DETAILED DESCRIPTION

In the following detailed description, reference is made to the accompanying drawings, that form a part hereof, and in which the specific embodiment, that may be practiced is shown by way of illustration. These embodiments are described in sufficient detail to enable those skilled in the art to practice the embodiment and it is to be understood that the logical, mechanical and other changes may be made without departing from the scope of the embodiment. The following detailed description is therefore not to be taken in a limiting sense.

Figure 1:
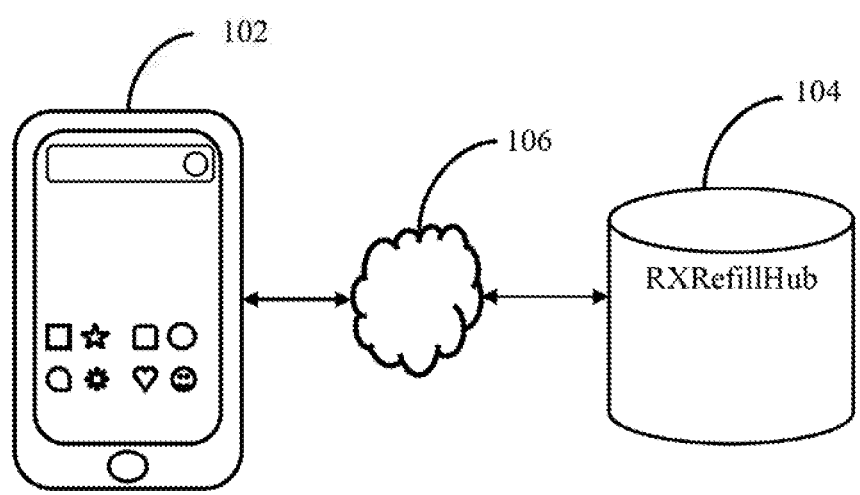
FIG. 1 illustrates a system-level diagram representative of a system facilitating transmission of Medicine prescriptions refills.

FIG. 1 illustrates a system diagram for the generation and transmission of Medicine prescription refill via a computing device 102. In accordance with the present disclosure, the healthcare provider generates and transmits medicine prescriptions (suggesting predetermined number of Medicine refills) via the computing device 102 to a server 104 (referred to as an 'RxRefillHub' hereafter). The computing device 102 communicates with the RxRefillHub 104 through a communication network 106. The examples of the communication network 106 include, but are not limited to the internet, an intranet, a radio frequency network, a telephone network, a satellite network. The healthcare provider also receives alerts via the computing device 102 and responds as indicated. The RxRefillHub 104 receives the Medicine prescriptions, subsequently stores the received prescription (refills), analyses the received prescriptions based on predetermined parameters, shares the results of analyses (of the medical prescriptions) with dispensing entities and generate alerts accessible to the concerned personnel via. RxRefillHub 104. The alerts generated by the RxRefillHub 104 include at least one of a refill alert, alerts at request of pharmacy, alerts at request of patient, formulary alerts, duplicate refill alert, non-compliance alerts (generated based on the disposition of refills).

Figure 2:
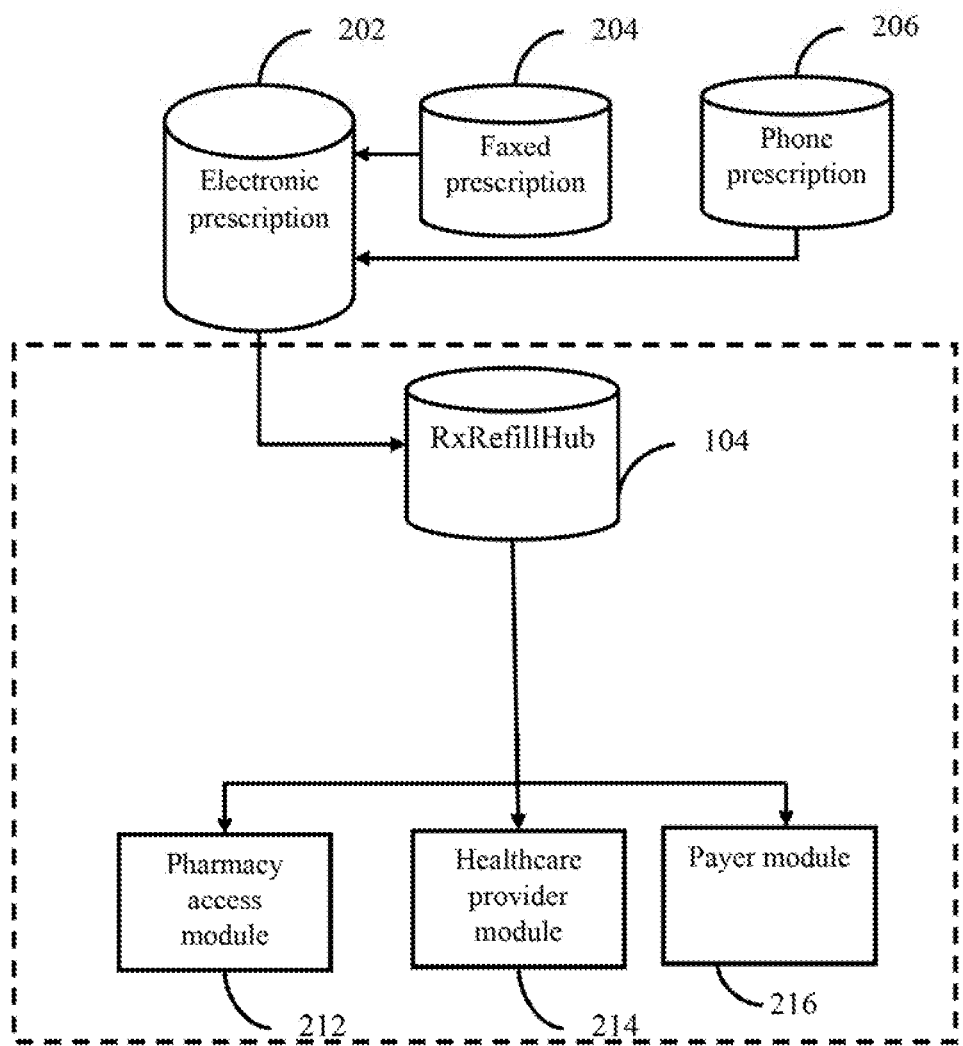
FIG. 2 illustrates a block diagram that outlines the functional components of RxRefillHub.

FIG. 2 illustrates a block diagram of the RxRefillHub 104 and the functional components that periodically interact with the RxRefillHub 104. Referring to FIG. 2, there is shown an Electronic prescription database 202, a Fax prescription database 204, a Phone prescription database 206, RxRefillHub 104, a Pharmacy access module 212, a Healthcare module 214 and a Payer module 216. The medical prescription is received through either an Electronic prescription database 202 or a Fax prescription database 204 or a Phone prescription database 206.

The RxRefillHub 104 is configured to accept and store the Medicine prescriptions refills received. According to an embodiment of the herein, the RxRefillHub 104 is a computer implemented system that stores and updates the Medicine prescriptions including refills received.

The RxRefillHub 104 fetches the data from the Electronic prescription database 202 and encrypts the data using a plurality of encryption techniques. According to an embodiment herein, the data is encrypted according to the compliance requirement of Health Insurance Portability and Accountability (HIPAA). The data received from the Electronic prescription database 202 is encrypted to ensure user privacy and prevent others from accessing the data without required permissions.

According to an embodiment herein, the RxRefillHub 104 receives a prescription for one month supply of medicines with one or more refills (for example, four refills). The RxRefillHub 104 transmits a first dispense instruction for a single refill to the pharmacy via a Pharmacy access module 212 (shown in FIG. 2), while storing the prescription for the three remaining refills. Once the Pharmacy access module confirms dispensing of the medication refill by a pharmacy, the RxRefillHub 104 transmits a second refill instruction to the Pharmacy access module for future processing. The aforementioned process is repeated until a predefined number of remaining refills (prescribed by a healthcare provider) at RxRefillHub 104 is achieved. Once the predefined number is reached, the RxRefillHub 104 generates an alert to refill medication or deletes the prescription or generates an alert indicative of the expiry of medicine prescription and transmits the alert to a healthcare provider. The alerts for initiating a refill or the alerts to Healthcare providers are generated based on parameters such as the patient's health condition, ongoing needs, side-effect profiles, drug interaction, and benefit versus risk ratio. The RxRefillHub 104 provides an alert to the Healthcare provider when the pending refills drop below the predefined number, thereby avoiding a delay in processing of prescriptions to provide continuous care to patients. Subsequently, the RxRefillHub 104 communicates with the Healthcare provider regarding the maintenance of prescribed therapy. Further, the RxRefillHub 104 provides an alert to the Healthcare provider in case of an update in drug formulary requiring a change in prescription.

According to an embodiment herein, the update in drug formulary generated by the RxRefillHub 104 is received by a Payer module 216 (shown in FIG. 2). The Payer module compares current prescription refills stored in the RxRefillHub 104 with the updated drug formulary to generate alerts for modification of prescription refills or generation of a new medication prescription. Thus, the Payer module in association with the RxRefillHub 104 helps in maintaining compliance with the prescribed therapy.

According to an embodiment herein, a new prescription refill received by the RxRefillHub 104 by a new Healthcare provider is analyzed by the RxRefillHub 104, for duplication of therapy, formulary adherence, drug interaction, patient's past experience on drug utilization. During analysis, each medicine mentioned in the prescription is checked for FDA-approved uses, contraindication, allergies, side effects, drug to drug interactions and warnings. After analyses, an alert is generated to the new Healthcare provider by the RxRefillHub 104. Further, when a prescription refill is not processed by a pharmacy due to patient non-compliance, a non-compliance alert is generated to a Healthcare provider. The non-compliance alert enables a provider or patient to determine the appropriateness of refill, improve compliance, and request appropriate changes in medication.

In accordance with an embodiment herein, in response to the alerts received from the RxRefillHub 104, the Healthcare provider performs at least one of the actions including adding a refill, deleting a stored refill, and modifying a stored refill.

The RxRefillHub 104 is a platform that analyses a plurality of responses to provide actionable insights required for understanding and analyzing a plurality of metrics to improve the safety of prescription refill, to improve communication, and to improve compliance. According to an embodiment herein, the RxRefillHub 104 fetches data front the Electronic prescription database 202, interacts with Payer Module 216, Pharmacy Access Module 212 and Healthcare provider module 214 to perform analysis based on a plurality of pre-determined parameters and guidelines. According to an embodiment herein, the plurality of parameters and guidelines are determined by responsible organizations such as Accountable Care Organization ACOs, Health Maintenance Organization HMOs, payers guidelines and best practices. The analytics also include predictive modeling using specific guidelines with metrics such as patient demographics, medical history and past medication usage of the patient, compliance issues, tolerability, effectiveness and side effects of drugs, formulary updates and availability of medicines to select an optimum treatment and generate medication plan. Based on the analysis, alerts are generated notifying benefits and risks involved in future treatment choices and Medicine prescription refills. The specific guidelines for initial treatment are based on respective disease state and its guiding associations. For example, the specific guidelines for diabetics care include guidelines from national and international diabetes association. In another example, communicable diseases care includes guidelines by world health organization and infectious disease association.

The Pharmacy access module 212 receives the data from the RxRefillHub 104. The Pharmacy access module 212 enables the patients to manage or route the prescription refills to their preferred pharmacies. The Pharmacy access module 212 generates alerts to the pharmacy about new prescriptions or refills for further processing. The Pharmacy access module 212 permits the pharmacies to receive the medicine prescriptions including one refill request at an instance, while storing the remaining refill requests in the RxRefillHub 104. The module generates alerts based on available refills to Healthcare providers, patient, and other concerned entities. Further, the RxRefillHub 104 communicates with the Pharmacy access module 212 regarding the formulary updates from insurance providers to enable addition, deletion, and modification of remaining refills.

The Healthcare provider module 214 receives alerts from RxRefillHub 104 about formulary updates, drug interactions and refill status. According to an embodiment herein, the alerts are based on the predetermined inputs assigned by the Healthcare provider. The alerts are received from a database on an electronic device of the Healthcare provider. The Healthcare provider module 214 also enables the healthcare providers to add, edit, and delete obsolete refills stored at RxRefillHub 104.

The Payer module 216 allows the update of payers' formularies for use by RxRefillHub 104. The Payer module 216 also provides medication associated risk monitoring system to all patients regardless of payer preferences and availability of funds. According to an embodiment herein, the RxRefillHub 104 provides a unified gateway to check a plurality of prescriptions associated with a patient and further monitor the risks and side effects posed by a combination of medicines. The Payer module 216 communicates with the RxRefillHub 104 to provide a unified gateway to perform checks and equilibrium test for at least one of the patient safety, workflow optimization (by improving coordination and communication), cost effective medication management by reducing wastage by inappropriate refills, errors in refills, and cost associated with side effects management from inappropriate use of medication.

According to an embodiment herein, the Payer module 216 continuously monitors updates in formulary from insurance providers. The formulary updates are communicated with the RxRefillHub 104 to generate alerts to a healthcare provider, patient, and pharmacies. Thus, the safety, reduced wastage and smart decision making by coordinating storage and release of refills by RxRefillHub 104.

According to an embodiment herein, the RxRefillHub 104 enables Healthcare providers to add, delete, modify refills before, prior to release to the Pharmacy access module, when a request for a refill (for a new or existing condition) is received from a patient. Further, the RxRefillHub 104 analyses the refills in a unified gateway when a prescription refill is generated, when Pharmacy access module 212 dispenses the refill, and when the formulary change results in an alteration in medication schedule.

Figure 3:
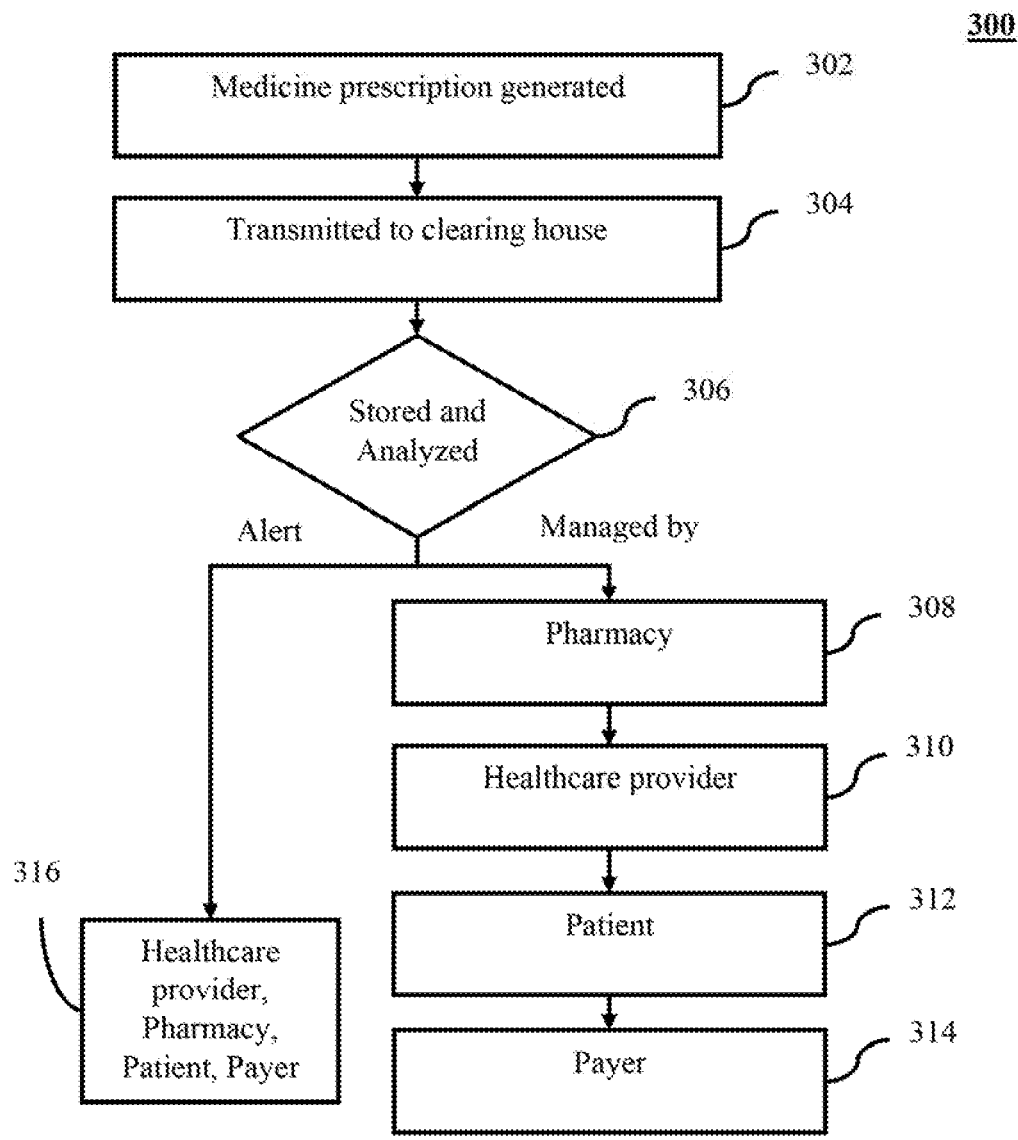
FIG. 3 illustrates a flowchart for Medicine prescriptions refill management via RxRefillHub.

FIG. 3 illustrates a flowchart for managing Medicine prescriptions refills using RxRefillHub 104 according to an embodiment herein. At first, the Medicine prescription refill is generated (Step 302). The Medicine prescription refill is generated through a plurality of modalities such as an electronic transmission, a fax, a phone and the like.

Once the Medicine prescription refill is generated, it is transmitted to the RxRefillHub (Step 304). The Medicine prescription and refills are stored and analyzed (Step 306). According to an embodiment, once the Medicine prescription refill is analyzed, an alert is generated for its further processing (Step 316). According to an embodiment herein, Medicine prescription refill is available to be updated or managed by a plurality of users (Step 308, 310, 312,314). According to an embodiment herein, the responses received are compliant with HIPAA. Further, the received responses are encrypted to ensure user privacy and security.

Advantageously, the embodiment herein provides a method and system for managing Medicine prescriptions refills. Further, the embodiment herein improves safety, and flexibility of Medicine prescriptions refills. Furthermore, the embodiment herein reduces wastage and enables smart decision making by coordinating storage and release of refills via an RxRefillHub. Also, the embodiment herein enables a Healthcare provider to, add, delete, modify refills prior to release to the Pharmacy access module, when a request for a refill (for a new or existing condition) is received from a patient.

The foregoing description of the specific embodiment will so fully reveal the general nature of the embodiment herein that others can, by applying current knowledge, readily modify and/or adapt for various applications such specific embodiment without departing from the generic concept, and therefore, such adaptations and modifications should and are intended to be comprehended within the meaning and range of equivalents of the disclosed embodiment. It is to be understood that the phraseology or terminology employed herein is for the purpose of description and not of limitation. Therefore, while the embodiment herein has been described in terms of preferred embodiment, those skilled in the art will recognize that the embodiment herein can be practiced with modifications.

What is claimed is:

1. A system comprising a hardware processor and a memory loaded with a set of instructions that are executed on the hardware processor for managing Medical prescriptions through one or more algorithms or software applications, said system comprising:
  a web-server communicably coupled to a computer based device, said web-server is configured to receive and store said Medical prescription refills through the one or more algorithms or software applications, said web-server is further configured to segregate and analyze each of the Medical prescriptions based on corresponding patient related information through the one or more algorithms or software applications, said web-server is further designed for configuring said medical prescriptions to be valid only for a predefined number of refills through the one or more algorithms or software applications, said web-server is further configured to transmit only one refill request associated with the medical prescriptions to the medical dispensaries at a time through the one or more algorithms or software applications, said web-server is further configured to automatically alert the dispensary and healthcare provider to modify or delete the Medical prescription through the one or more algorithms or software applications, when the predefined number of refills are completed;
  Healthcare Provider module loaded on a computer device and run on a hardware processor to access said healthcare provider via the computer enabled device to receive medicine prescriptions suggesting a predetermined number of medicine refills through the one or more algorithms or software applications, and wherein said Healthcare Provider module is configured for storing information pertinent to at least formulary updates, drug interactions and refill status corresponding to each of the medical prescriptions through the one or more algorithms or software applications, said information pertinent to at least formulary updates, drug interactions and refill status generated by said web-server through the one or more algorithms or software applications, and wherein said Healthcare Provider module is configured to generate alerts corresponding to at least one of formulary updates, drug interactions and refill status corresponding to each of the medical prescriptions through the one or more algorithms or software applications, and wherein said Healthcare Provider module is further configured to enable the healthcare provider to selectively modify the medical prescriptions stored at the web-server through the one or more algorithms or software applications; and
  a Payer module loaded on a computer device and run on a hardware processor to generate and selectively update formularies corresponding to patients through the one or more algorithms or software applications, based on the corresponding patient related information, and wherein said Payer module is still further configured to identify risks associated with medications specified in said medical prescriptions, and inform said patients of said risks, regardless of payer preferences (formulary) and availability of funds through the one or more algorithms or software applications, and wherein the Payer module is further configured to compare current prescription refills stored in the web-server with the updated drug formulary to generate alerts for modification of prescription refills or generation of a new medication prescription through the one or more algorithms or software applications, thereby maintaining compliance with a prescribed therapy (formulary changes), and wherein the Payer module is configured to communicate with the web-server to provide a unified gateway to perform checks and equilibrium tests for at least one of a patient safety, a workflow optimization, and cost control management by reducing wastage by inappropriate bills (prescription), error in refills, duplicate refill, and cost associated with side effect management from inappropriate use of medication through the one or more algorithms or software applications, and wherein the Payer module is further configured to monitor updates in formulary from insurance providers to generate alerts to the healthcare provider, patient and pharmacies through the one or more algorithms or software applications.

2. The system as claimed in claim 1, further comprises a Pharmacy Access module loaded on the computer system, and wherein said Pharmacy Access module is run on the hardware processor and configured to receive the medical prescriptions, and render said medical prescriptions to be accessed by corresponding patients via a web based device through the one or more algorithms or software applications, and wherein said Pharmacy Access module is still further configured to enable the patients to electronically transmit the medical prescriptions for only one refill, to preferred medical dispensaries through the one or more algorithms or software applications.

3. The system as claimed in claim 2, wherein said Pharmacy Access module is still further configured to generate alerts to be transmitted to medical dispensaries about availability of new medical prescriptions and new refills due through the one or more algorithms or software applications.

4. A computer implemented method comprising instructions stored on a non-transitory computer readable storage medium and executed on a computer system provided with a hardware processor and memory for managing medical prescriptions through one or more algorithms or applications, said method comprising the steps of:

receiving the medical prescriptions from the computer based device to a web-server, and storing transmitted medical prescriptions on the web-server through the one or more algorithms or software applications;

analyzing each of medical prescriptions and determining the number of refills associated with each of the Medical prescriptions with the web-server through the one or more algorithms or software applications;

configuring each of said medical prescriptions to be dispended only one refill at a time, and transmit configured Medical prescriptions to predetermined medical dispensaries for disposal with the web-server through the one or more algorithms or software applications;

causing said web-server to retransmit said medical prescriptions for another refill only after expiry of a validity period associated with an earlier refill specified by each of medical prescriptions through the one or more algorithms or software applications;

enabling the healthcare provider to review alerts of at least formulary updates, drug interactions and refill status corresponding to each of the medical prescriptions, and transmit said formulary updates, drug interactions and refill status in the form of alerts to patients identified by corresponding medical prescriptions with a Healthcare Provider module, through the one or more algorithms or software applications with a Payer module loaded on the computer system;

analyzing each of the medical prescriptions and identifying risks associated with medication prescribed via said medical prescriptions, and transmitting information pertinent to said risks, in the form of alerts to the patients through the one or more algorithms or software applications with a Payer module loaded on the computer system; and wherein the Payer module loaded on the computer system and nm on a hardware processor is configured to generate and selectively update formularies corresponding to patients through the one or more algorithms or software applications, based on the corresponding patient related information, and wherein said Payer module is further configured to identify risks associated with medications specified in said medical prescriptions, and inform said patients of said risks, regardless of payer preferences (formulary) and availability of funds through the one or more algorithms or software applications, and wherein the Payer module is further configured to compare current prescription refills stored in the web-server with the updated drug formulary to generate alerts for modification of prescription refills or generation of a new medication prescription through the one or more algorithms or software applications, thereby maintaining compliance with a prescribed therapy (formulary changes), and wherein the Payer module is configured to communicate with the web-server to provide a unified gateway to perform checks and equilibrium tests for at least one of a patient safety, a workflow optimization, and cost control management by reducing wastage by inappropriate bills (prescription), error in refills, duplicate refills, and cost associated with side effect management from inappropriate use of medication-through the one or more algorithms or software applications, and wherein the Payer module is further configured to monitor updates in formulary from insurance providers to generate alerts to the healthcare provider, patient and pharmacies through the one or more algorithms or software applications.

5. The method as claimed in claim 4, further includes the step of providing emergency and urgent care providers, a secure and compliant access to patients' current prescription status and past refill history through the one or more algorithms or software applications.

* * * * *